United States Patent [19]

Nachbur et al.

[11] Patent Number: 4,487,800
[45] Date of Patent: Dec. 11, 1984

[54] PROCESS FOR FIREPROOFING ORGANIC FIBRE MATERIAL USING PHOSPHONIC ACID SALTS

[75] Inventors: Hermann Nachbur, Reinach; Christian Guth, Basel, both of Switzerland

[73] Assignee: Ciba-Geigy Corporation, Ardsley, N.Y.

[21] Appl. No.: 527,545

[22] Filed: Aug. 29, 1983

Related U.S. Application Data

[62] Division of Ser. No. 342,880, Jan. 26, 1982, Pat. No. 4,452,849.

[30] Foreign Application Priority Data

Feb. 3, 1981 [CH] Switzerland ............... 700/81

[51] Int. Cl.$^3$ .................. B32B 7/00; B05D 3/02
[52] U.S. Cl. .................. 428/265; 252/8.8; 260/501.14; 427/389.9; 427/392; 427/393.3; 428/260; 428/264; 428/272; 428/276
[58] Field of Search ............ 427/393.3, 389.9, 392; 252/8.8; 260/501.14; 428/264, 265, 260, 272, 276

[56] References Cited

U.S. PATENT DOCUMENTS

| | | | |
|---|---|---|---|
| 4,097,560 | 6/1978 | Littman et al. | 427/393.3 X |
| 4,104,172 | 8/1978 | Smith et al. | 427/393.3 X |
| 4,151,322 | 4/1979 | Rosenthal et al. | 427/393.3 X |

FOREIGN PATENT DOCUMENTS 49-093321  9/1974  Japan .................. 260/501.14

Primary Examiner—Thurman K. Page
Attorney, Agent, or Firm—Edward McC. Roberts

[57] ABSTRACT

Novel phosphonic acid salts produced from ethane- or methanephosphonic acid, dicyandiamide and/or guanidine and optionally ammonia and corresponding to the formula

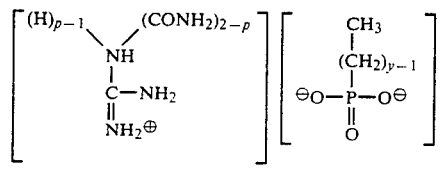

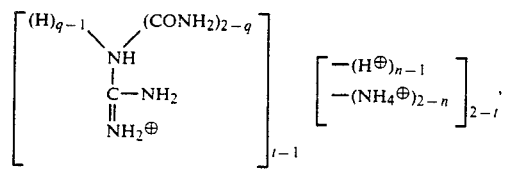

wherein n, p, q, t and y are each 1 or 2, are particularly suitable for fireproofing organic fibre materials. Synthetic and/or cellulose-containing fibre materials are treated with an aqueous solution of the phosphonic acid salts and are then dried preferably at 60° to 200° C. The applied phosphonic acid salts impair only negligibly the textile-mechanical properties of the treated fibre materials, especially of the cellulose-containing fibre materials dried at 120° to 150° C.

6 Claims, No Drawings

PROCESS FOR FIREPROOFING ORGANIC FIBRE MATERIAL USING PHOSPHONIC ACID SALTS

This is a divisional of application Ser. No. 342,880 filed on Jan. 26, 1982, now U.S. Pat. No. 4,452,849.

The present invention relates to novel phosphonic acid salts, to processes for producing them, and to their use as fireproofing agents for organic fibre material, and also to an application process for fireproofing organic fibre materials by use of the novel phosphonic acid salts, to an aqueous solution containing the novel phosphonic acid salts, as an agent for carrying out the application process, and to the fibre materials fireproofed by the process according to the invention.

The phosphonic acid salts according to the invention correspond to the formula

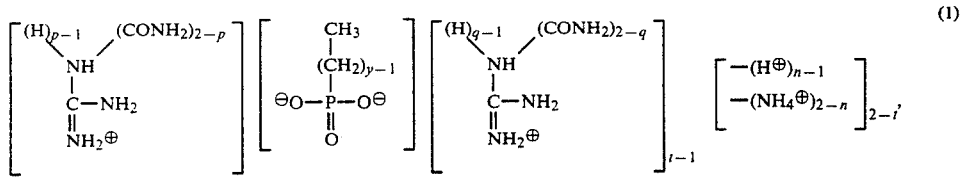

(1)

wherein n, p, q, t and y are each 1 or 2.

When t in the formula (1) is 2, the phosphonic acid salts correspond to the formula

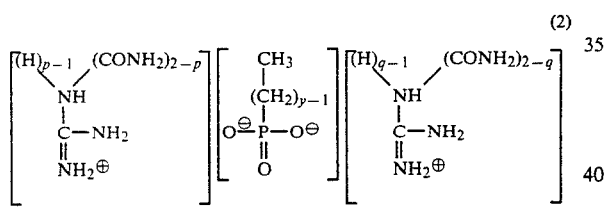

(2)

wherein p, q and y are each 1 or 2.

When p and q in the formula (2) differ from one another, that is to say, when p is 1 and q is 2, or when p is 2 and q is 1, the phosphonic acid salts correspond to the formula

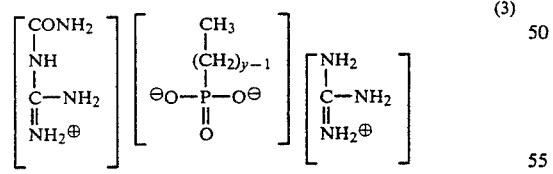

(3)

wherein y is 1 or 2, but preferably 1.

Preferred therefore is the phosphonic acid salt of the formula

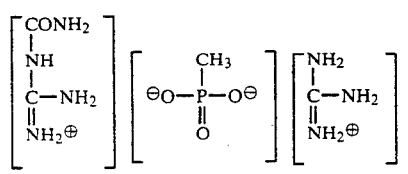

(4)

When on the other hand p and q in the formula (2) have the same meaning, the phosphonic acid salts, if p and q are 2, correspond to the formula

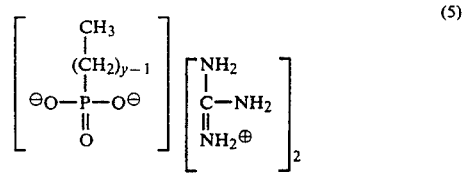

(5)

wherein y is 1 or 2, but preferably 1.

Preferred therefore is the phosphonic acid salt of the formula (6)

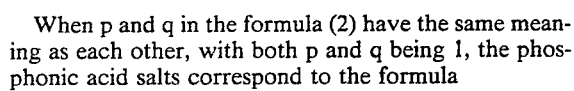

When p and q in the formula (2) have the same meaning as each other, with both p and q being 1, the phosphonic acid salts correspond to the formula

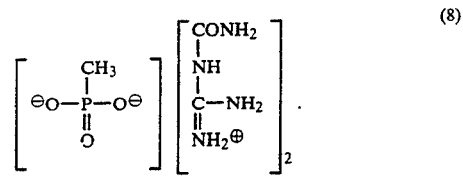

(7)

wherein y is 1 or 2, but preferably 1.

Preferred therefore is the phosphonic acid salt of the formula (8)

When in the formula (1) t is 2, and p and q have the same meaning as each other, p and q are preferably 1. Thus the phosphonic acid salts of the formulae (5) and in particular (6) are preferred to the phosphonic acid salts of the formulae (7) and (8). Of the phosphonic acid salts of the formula (1) in which t is 2, the salts of special interest are those of the formula (3) and particularly (4), as well as the salts of the formula (5) and especially (6).

When t in the formula (1) is 1, the phosphonic acid salts correspond to the formula

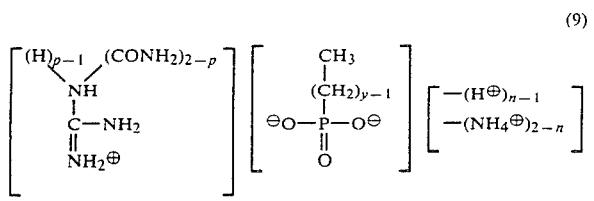

(9)

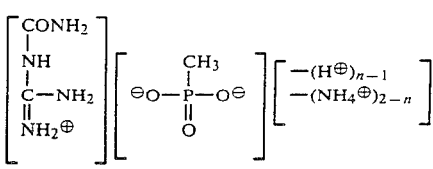

(15)

wherein n, p and y are each 1 or 2.

When p in the formula (9) is 2, the phosphonic acid salts correspond to the formula wherein n is 1 or 2.

When n in the formula (15) is 1, the phosphonic acid salt concerned corresponds to the formula

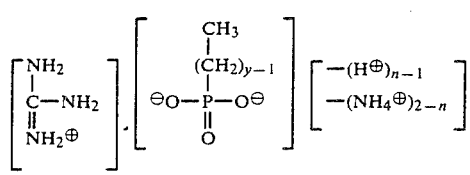

(10)

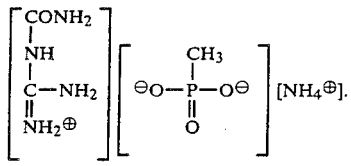

(16)

wherein n and y are each 1 or 2.

In the formula (10), y is preferably 1. Preferred phosphonic acid salts thus correspond to the formula

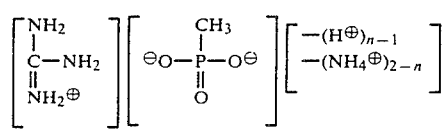

(11)

When however n in the formula (15) is 2, the phosphonic acid salt in question corresponds to the formula

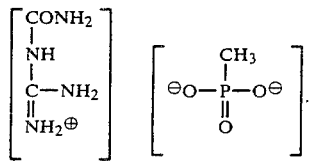

(17)

wherein n is 1 or 2.

When n in the formula (11) is 1, the phosphonic acid salt concerned corresponds to the formula

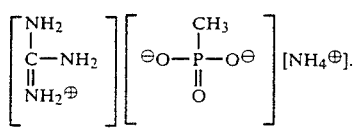

(12)

When t in the formula (1) is 1, n is preferably 2 and p is preferably 1. Among the phosphonic acid salts of the formula (1) wherein t is 1, the salts of the formulae (14), (15), (16) and (17) are preferred to the salts of the formulae (10), (11), (12) and (13), the salt of the formula (13) and particularly the salt of the formula (17) being of greatest interest.

The phosphonic acid salts according to the invention are produced, using methods known per se, by reaction of the corresponding phosphorus-containing acids with the appropriate nitrogen-containing bases. The process for producing the phosphonic acid salts of the formula (1) comprises reacting in an aqueous medium, optionally at elevated temperature, 1 mol of phosphonic acid of the formula When however n in the formula (11) is 2, the phosphonic acid salt in question corresponds to the formula

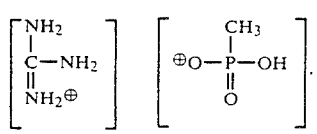

(13)

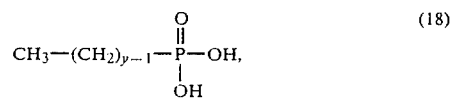

(18)

When p in the formula (9) is 1, the phosphonic acid salts correspond to the formula wherein y is 1 or 2, with 1 mol of a nitrogen compound of the formula

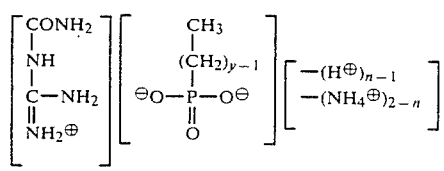

(14)

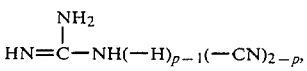

(19)

wherein p is 1 or 2, and 1 mol of a nitrogen compound of the formula wherein n and y are each 1 or 2.

In the formula (14), y is preferably 1. Preferred phosphonic acid salts thus correspond to the formula

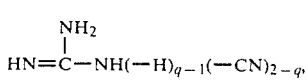

(20)

wherein q is 1 or 2, when t in the formula (1) is 2, or with 1 mol of a nitrogen compound of the formula (19) and optionally 1 mol of ammonia when t in the formula (1) is 1, the nitrogen compound being present as free guanidine, or preferably as guanidine carbonate, when p and q in the formulae (19) and (20) are 2, and the reaction being performed with the addition of 1 mol of water when p and q are 1, or being performed with removal of 1 mol of carbon dioxide when guanidine carbonate is used.

In the case of the starting compound of the formula (18), this is, depending on the meaning of y, ethane- or preferably methanephosphonic acid, which is described for example in J. Am. Chem. Soc. 75, 3379 ff (1953); and in the case of the starting compounds of the formulae (19) and (20), these are dicyandiamide when p and q are 1, and guanidine when p and q are 2.

Where dicyandiamide is used, there occurs in the reaction, as already mentioned, an addition of water. The reaction with dicyandiamide is preferably performed at elevated temperature, for example at 60° to 100° C., and preferably between 85° and 95° C. Also higher reaction temperatures of, for example, 100° to 130° C., are suitable provided that the reaction with dicyandiamide is carried out under pressure.

In the reactions with guanidine, the salt thereof is preferably used, namely guanidine carbonate, since guanidine salts are more readily available than free guanidine. For practical reasons, only guanidine carbonate is suitable as salt, because the corresponding weak acid, that is, carbonic acid, does not participate in the reaction but is removed, under the applied conditions, as carbon dioxide from the reaction mixture, in contrast to the free acids of the guanidine salts of a different kind, such as guanidine hydrochloride or guanidine acetate. With the use of guanidine carbonate, there is taken into account with respect to the molar ratios stated in the foregoing the fact that 2 mols of free guanidine are present per mol of guanidine carbonate. The reactions with guanidine or with the carbonate thereof are optionally performed at elevated temperature, for example at 20° to 100° C., preferably at 20° to 60° C., and particularly at 40° to 60° C. Where guanidine carbonate is used, a temperature of 40° to 60° C. is especially desirable in order to accelerate the evolution of carbon dioxide. The removal of carbon dioxide from the reaction mixture can be completed or accelerated under reduced pressure, suitable temperatures in this case being between 20° and 40° C.

The reaction with ammonia occurs only when n and t in the formula (1) are both 1. In this case, the ammonia is preferably used in the form of an aqueous solution. The optional reactions with ammonia are performed preferably at 20° C. or at the slightly elevated temperature of 20° to 40° C.

The sequence in which the starting components are reacted is of decisive importance. For the reaction with dicyandiamide alone, the phosphonic acid is placed into the reaction vessel and subsequently reacted with dicyandiamide, whereas for the reaction with guanidine alone, the preferred procedure is to place guanidine carbonate in the reaction vessel and to then react it with the phosphonic acid. When both dicyandiamide and guanidine are used, phosphonic acid is placed into the reaction vessel, and reacted firstly with dicyandiamide and lastly with guanidine or preferably with guanidine carbonate. Where the optional reaction with ammonia is carried out, the ammonia is preferably added last if dicyandiamide is used, whilst with use of guanidine, the phosphonic acid is firstly reacted with ammonia and finally with guanidine or preferably with guanidine carbonate.

To produce the phosphonic acid salts of the formula (2), the procedure is to react 1 mol of ethane- or methanephosphonic acid with 2 mols of dicyandiamide or 1 mol of guanidine carbonate where p and q in the formula (2) have the same meaning, or with 1 mol of dicyandiamide and 0.5 ml of guanidine carbonate where p and q in the formula (2) differ from one another.

The phosphonic acid salts of the formulae (3) and (4) are produced by reacting 1 mol of ethane- or particularly methanephosphonic acid with 1 mol of dicyandiamide at 60° to 100° C., and subsequently with 0.5 mol of guanidine carbonate at 20° to 60° C.; the phosphonic acid salts of the formulae (5) and (6) are produced by reacting 1 mol of guanidine carbonate with 1 mol of ethane- or preferably methanephosphonic acid at 20° to 60° C.; and the phosphonic acid salts of the formulae (7) and (8) are produced by reacting 1 mol of ethane- or preferably methanephosphonic acid with 2 mols of dicyandiamide at 60° at 100° C.

To produce the phosphonic acid salts of the formula (9), 1 mol of ethane- or methanephosphonic acid is reacted with 1 mol of dicyandiamide where p in the formula (9) is 1, or with 0.5 mol of guanidine carbonate where p in the formula (9) is 2, and 1 mol of an aqueous ammonia solution where n in the formula (9) is 1.

The phosphonic acid salts of the formulae (10) and (11) are produced with the use of guanidine carbonate by an analogous procedure.

To produce the phosphonic acid salt of the formula (12), 1 mol of methanephosphonic acid is reacted with 1 mol of an aqueous ammonia solution and subsequently with 0.5 mol of guanidine carbonate; and to produce the phosphonic acid salt of the formula (13), 0.5 mol of guanidine carbonate is reacted with 1 mol of methanephosphonic acid at 20° to 60° C.

The phosphonic acid salts of the formulae (14) and (15) are produced using dicyandiamide with an analogous procedure.

To produce the phosphonic acid salt of the formula (16), 1 mol of methanephosphonic acid is reacted with 1 mol of dicyandiamide at 60° at 100° C., and subsequently with 1 mol of an aqueous ammonia solution at 20° to 60° C., and to produce the phosphonic acid salt of the formula (17), the procedure is carried out as just described except however that the ammonia solution is not used.

The application process according to the invention for fireproofing organic fibre material, whereby the phosphonic acid salts of the formula (1) are used as fireproofing agents, comprises treating this material with an aqueous solution of at least one phosphonic acid salt of the formula (1) and subsequently drying the treated material.

In this process, the treatment of the fibre material is in general carried out using the spraying and especially padding methods. Also suitable is for example the immersion method, or preferably the slop-padding method.

Since the phosphonic acid salts of the formula (1) are water-soluble, additions of auxiliaries for promoting solubility in the application baths and liquors or spray solutions are as a rule not necessary. Customary softening agents or surface-active agents can however with advantage be concomitantly used.

In the preferred padding process, the phosphonic acid salt solutions are applied, with a liquor absorption of for example 60 to 110, preferably 60 to 100, particularly 65 to 80, percent by weight, to the fibre material to be finished, and the impregnated material is subsequently dried, as a rule at temperatures of 60° to 200° C., preferably however at most at 150° C., for example between 60° and 150° C. and especially between 120° and 150° C.

The process according to the invention is suitable for fireproofing organic fibre materials, including wood, but preferably paper, and for example carpets, or particularly textiles in any stage of processing, such as filaments, yarns, spools, fleeces, knitted goods, fabrics or finished articles of clothing, or furnishing fabrics, such as carpets, furniture coverings, curtains or fabric-covered carpets.

The organic fibre material to be finished can be of natural or synthetic origin, or can consist of mixtures of natural and synthetic fibres. Suitable natural fibres are especially keratin- or cellulose-containing fibres, including fibres made from regenerated cellulose, such as linen, hemp, sisal or ramie fibres, and preferably wool and cotton fibres, and/or artificial silk, rayon staple or viscose fibres.

Also suitable in addition to pure cellulose fibres are mixtures thereof with synthetic fibres, the proportion of cellulose being preferably 20 to 80 percent by weight of the mixture. Synthetic fibres which can be treated are for example polyesters, preferably acrylonitrile copolymers, and in particular polyacrylonitrile. Applicable also, although less preferred, are fibres formed from cellulose acetate, for example cellulose-2½-acetate and cellulose triacetate, and fibres made from crosslinked polyvinyl alcohols, for example acetates or ketals of polyvinyl alcohols.

Of primary interest, besides cellulose fibres and mixtures thereof with synthetic fibres, are however pure synthetic fibre materials, especially those made from polyester or in particular polyacrylonitrile or acrylonitrile copolymers. Polyacrylonitrile carpets can be particularly well fireproofed according to the invention. Such polyester fibres are derived especially from terephthalic acid, for example from poly-(ethylene glycol terephthalate) or from poly-(1,4-cyclohexylenedimethylene terephthalate). In the case of the acrylonitrile copolymers, the proportion of acrylonitrile is advantageously at least 50, preferably at least 85, percent (by weight) of the copolymer. They are above all copolymers for the producing of which other vinyl compounds, for example vinyl chloride, vinylidene chloride, methyl acrylates, acrylamide or styrenesulfonic acids, have been used as comonomers.

The aqueous solutions, with which the said fibre materials are treated, contain as a rule, as the agent for carrying out the application process according to the invention, 25 to 500 g of a phosphonic acid salt of the formula (1) per liter, and optionally customary additives, such as the softening agents or surface-active agents (tensides) mentioned in the foregoing. Particularly in the treatment of purely synthetic fibre materials, for example those made from polyester, by use of the preferred padding method, bath concentration of 25 to 100 g/l suffice, especially when ammonium salts are present in the bath. Preferably, however, bath concentrations of 200 to 450 g/l are used in the padding process, in particular when a fireproof finish is being imparted to polyacrylonitrile fibres. The pH-value of the solutions used according to the invention is generally 3 to 9.

The necessary coating with a compound of the formula (1) for obtaining an adequate fireproofing effect varies depending on the type of fibres and material, and is as a rule between 2 and 40%, relative to the weight of fibres.

Permanent fireproofing effects are not obtained by the process according to the invention, so that consequently the treated fibre materials should not undergo any subsequent washing treatment. The process according to the invention is characterised above all in that the most varied types of substrates can be effectively fireproofed by this process.

The fastness to light of dyed or brightened fibre materials is virtually unaffected by the coatings according to the invention. Furthermore, the good compatibility of the phosphonic acid salts, used according to the invention, with most textile finishing agents, such as with water- and oil-repellent agents or stiffening and softening agents, is especially advantageous. The small deposited amounts necessary for fireproofing polyester fibres are an additional advantage of the process according to the invention.

The most significant advantage of the present invention, however, is that the fibre materials can be dried not only at the usual drying temperatures of up to 100° C. but also at higher temperatures, for example between 100° and 200° C., especially between 120° and 150° C., without the mechanical properties of the fibre materials dried in this manner, such as handle, hygroscopicity and tearing strength, becoming greatly impaired. In particular, the fibre materials treated according to the invention are less inclined to yellow at high drying temperatures than are fibre materials fireproofed by methods hitherto known. With drying at elevated temperature, the drying time is all the shorter the higher the temperature. A drying time of ½ to 1 minute is as a rule sufficient at 200° C., whilst at 140° to 160° C. 2 to 10 minutes are generally required. The saving in time as a result of the shortened drying time enables a higher capacity of the finishing plants to be achieved. This drying at elevated temperature, also denoted as "overdrying" can be carried out in practice using nozzle dryers of conventional design.

Particularly cellulose-containing fibre materials tend on being subjected to overdrying to yellow and to undergo disadvantageous changes with respect to their textile-mechanical properties. In contrast to the fireproofing agents hitherto used, particularly known phosphonic acid salts, the phosphonic acid salts according to the invention surprisingly enable the yellowing and impairment of the textile-mechanical properties, even with overdrying of, in particular, cellulose-containing fibre materials, to be largely eliminated.

Accordingly, cellulose fibres can be impregnated in the application process according to the invention, using the padding method, with an aqueous solution of a phosphonic acid salt of the formula (1), and subsequently dried at 120° to 150° C.

The values given in the following Examples for "parts" and percentages relate to weight.

PRODUCTION EXAMPLES

Example 1

986 parts of a 97.4% methanephosphonic acid (10 mols) are dissolved in 1800 parts of de-ionised water at 20° C., and the solution is heated to 90° C. In the course of 30 minutes, 840 parts of dicyandiamide (10 mols) are added at 90° C. to the methanephosphonic acid solution, the reaction mixture being occasionally cooled. The reaction mixture is subsequently held at 90° C. for 90 minutes and then cooled to 20° C. There are thus obtained 3594 parts of an aqueous, colourless, clear solution having a pH-value of 3.0, and a content of phosphonic acid salt of the formula (17) of 48.0% (87.1% of theory) and of unreacted methanephosphonic acid of 4.2% (15.5% of the amount used), the stated contents of salt and acid being determined by virtue of titration of a specimen of the reaction solution with an aqueous sodium hydroxide solution.

A portion of the aqueous solution obtained is concentrated under reduced pressure at a temperature of at most 50° C., and subsequently dried at 50° C. under reduced pressure. 200 parts of the dried crude substance thus obtained are freed from the unreacted methanephosphonic acid by being washed three times at 20° C. with 200 parts of isopropanol each time, and then dried at 50° C. under reduced pressure. The crude substance purified in this manner has a melting point of 151° C. and a content of phosphonic acid salt of the formula (17) of 95.8%. This purified crude substance is free from unreacted methanephosphonic acid.

For the purpose of analysis, 10 parts of the resulting crude substance are recrystallized in 400 parts of 95% ethanol. The recrystallised pure substance is in the form of white powder and has a melting point of 163° C.

Elementary analysis of the recrystallised pure substance: calculated: C 18.18%, H 5.55%, N 28.29%, P 15.65%; found: C 18.2%, H 5.4%, N 28.3%, P 15.4%.

Example 2

46 parts of a 25% aqueous ammonia solution (0.68 mol) is added at 20° C. within 20 minutes, with occasional cooling of the reaction mixture, to 207 parts of the aqueous solution obtained in Example 1, which has a content of 48% of phosphonic acid of the formula (17) (0.5 mol) and of 4.2% of free methanephosphonic acid (0.09 mol). The result is 253 parts of a cloudy aqueous solution, which is subsequently filtered. The now clear solution contains 42% (100% of theory) of phosphonic acid of the formula (16) and 4.6% of methanephosphonic acid diammonium salt.

A part of the aqueous solution obtained is concentrated at a maximum of 50° C. under reduced pressure, and then dried at 50° C. under reduced pressure. The crude substance thus obtained melts at 90° to 125° C. with decomposition (evolution of ammonia), and gives the following elementary analysis:
calculated: C 16.75%, H 6.56%, N 32.55%, P 14.40%; found: C 16.6%, H 6.4%, N 29.7%, P 14.1%.

Example 3

A solution of 124 parts of a 99% guanidine carbonate (0.68 mol) in 2150 parts of de-ionised water is added at 50° C. within 30 minutes to 413 parts of the aqueous solution obtained in Example 1, which solution contains 48% of phosphonic acid of the formula (17) (1 mol) and 4.2% of free methanephosphonic acid (0.18 mol). The reaction mixture is kept at this temperature for 30 minutes until the evolution of $CO_2$ has finished, and the reaction mixture is subsequently cooled to 20° C. The yield is 2656 parts of a colourless, clear aqueous solution containing 9.68% (100% of theory) of phosphonic acid salt of the formula (4) and 1.45% of phosphonic acid salt of the formula (6).

A portion of the aqueous solution obtained is concentrated at a temperature of at most 50° C. under reduced pressure, and subsequently dried at 50° C. under reduced pressure. 10 parts of the crude substance thus obtained are recrystallised in 100 parts of ethanol and 35 parts of water. There is obtained as recrystallised substance the phosphoric acid salt of the formula (4), which melts at 298° to 300° C. with decomposition and gives the following elementary analysis:
calculated: C 17.44%, H 6.62%, N 35.59%, P 11.24%; found: C 17.9%, H 7.1%, N 35.6%, P 11.2%.

Example 4

A solution of 512.5 parts of a 93.7% methanephosphonic acid (5 mols) in 100 parts of de-ionised water is added at 20° C., within 15 minutes, to a solution of 455 parts of a 99% guanidine carbonate (2.5 mols) in 1000 parts of di-ionised water, in the course of which the reaction mixture warms up to 25° C. The reaction mixture is then heated to 50° C.; it is held at this temperature for 30 minutes, and subsequently concentrated at 50° C. under reduced pressure to obtain 1550 parts of a clear, colourless aqueous solution containing 50% (100% of theory) of the phosphonic acid salt of the formula (13).

A portion of the aqueous solution thus obtained is concentrated at a temperature of at most 50° C. under reduced pressure, and then dried at 50° C. under reduced pressure. Ten parts of the crude substance obtained are recrystallised in 200 parts of absolute ethanol; the recrystallised substance has a melting point of 125° to 129° C. and gives the following elementary analysis:
calculated: C 15.49%, H 6.50%, N 27.09%, P 19.97%; found: C 15.7%, H 6.6%, N 26.9%, P 19.9%.

Example 5

A solution of 51.25 parts of a 93.7% methanephosphonic acid (0.5 mol) in 100 parts of de-ionised water is added at 20° C., within 20 minutes, to a solution of 91 parts of a 99% guanidine carbonate (0.5 mol) in 200 parts of de-ionised water, in the course of which the reaction mixture warms up to 27° C. It is then heated to 50° C.; it is subsequently held at this temperature for 30 minutes, concentrated at a maximum of 55° C. under reduced pressure, and afterwards dried at 50° C. under reduced pressure. The yield is 106 parts of the phosphonic acid salt of the formula (6) (99% of theory), which is in the form of a white crystalline substance, which does not melt until 250° C.

Elementary analysis: calculated: C 16.83%, H 7.06%, N 39.24%, P 14.46%; found: C 18.8%, H 6.8%, N 37.5%, P 14.7%.

Example 6

34 parts of a 25% aqueous ammonia solution (0.5 mol) are added, within 5 minutes, to a solution of 48.35 parts of a 99.3% methanephosphonic acid (0.5 mol) in 200 parts of de-ionised water, in the course of which the temperature of the reaction mixture rises to 40° C. After completion of the addition of ammonia, there is added to the reaction mixture, within 5 minutes, a solution of 45.5 parts of a 99% guanidine carbonate (0.25 mol) in 200 parts of de-ionised water, during which time the temperature of the reaction mixture falls to 30° C. The resulting aqueous opal-cloudy solution is concentrated at a maximum of 50° C. under reduced pressure, and subsequently dried at 40° C. under reduced pressure. The yield is 83 parts (96.4% of theory) of the phosphonic acid salt of the formula (12), which is in the form of a white crystalline substance, which melts at 137° C. with decomposition.

Elementary analysis: calculated: C 13.96%, H 7.62%, N 32.54%, P 18.00%; found: C 14.2%, H 6.9%, N 29.3%, P 18.8%.

Example 7

59.15 parts of a 97.4% methanephosphonic acid (0.6 mol) are dissolved in 292 parts of de-ionised water at 20° C., and the solution is heated to 90° C. To this methanephosphonic acid solution are then added at 90° C. within 15 minutes, with occasional cooling of the reaction mixture, 100.8 parts of dicyandiamide (1.2 mols). The reaction mixture is subsequently held at 97° C. for 15 hours, and then cooled to 20° C. After a water-insoluble by-product formed during the reaction (33 parts of dry substance) has been filtered off, there remain 390 parts of a colourless, clear aqueous solution containing 38% (82.3% of theory) of the phosphonic acid salt of the formula (8).

A portion of the aqueous solution obtained is concentrated at a temperature of at most 50° C., and subsequently dried at 50° C. under reduced pressure. The crude substance thus obtained melts from 155° C., with decomposition, and gives the following elementary analysis:

calculated: C 20.00%, H 5.71%, N 37.33%, P 10.32%; found: C 18.9%, H 5.9%, N 36.6%, P 10.4%.

Example 8

135.8 parts of a 81% ethanephosphonic acid (1 mol) are dissolved in 150 parts of de-ionised water at 20° C., and the solution is heated to 85° C. There are then added to the ethanephosphonic acid at 85° C., within 30 minutes, 84 parts of dicyandiamide (1 mol); and after completion of the addition, the temperature of the reaction mixture rises automatically within 10 minutes to 92° C. The reaction mixture is subsequently held at 85°-90° C. for 1½ hours, and is then cooled to 20° C. The yield is 372 parts of an aqueous, clear colourless solution, which is concentrated at 60°-65° C. under reduced pressure. There are thus obtained, as crude substance, 232 parts (100% of theory) of a partially crystallised white product containing 20 parts of water. This product is recrystallised in 300 parts of 95% ethanol to obtain 79.5 parts of the recrystallised pure substance of the formula (14) wherein y and n are 2: this substance is in the form of a crystalline white powder which melts at 163° to 164° C., with decomposition, and gives the following elementary analysis:

calculated: C 22.76%, H 5.73%, N 26.54%, P 14.67%; found: C 22.8%, H 6.0%, N 26.4%, P 14.6%.

APPLICATION EXAMPLES

Example 9

Various fabrics are padded with an aqueous liquor of the composition given in the following Table I, and then dried at 80° C. for 30 minutes. After drying, a test to determine the fireproofing effect is carried out according to DOC FF 3-71 (burning time 3 seconds). An assessment of the effect the fireproofing finish has on the handle is carried out after drying of the respective fabric. Handle is assessed on the basis of a scale of ratings from 0 to 4, the best rating 0 corresponding to the untreated fabric, and the poorest rating 4 to an undesirable stiff handle.

All the test results are summarised in the following Table I.

TABLE I

| | Type and weight per unit area of the fabric | | | | | |
| --- | --- | --- | --- | --- | --- | --- |
| | cotton (140 g/m²) | | polyacrylo-nitrile (138 g/m²) | | polyester/cotton 50:50 (167 g/m²) | |
| | treated | un-treated | treated | un-treated | treated | un-treated |
| g of 48% aqueous solution of the salt of the formula (17) according to Example 1 per liter of liquor | 166 | 0 | 702 | 0 | 694 | 0 |
| % of coating of salt of the formula (17) after drying | 6.6 | — | 37.0 | — | 22.1 | — |
| fireproofness | | | | | | |
| burning time (sec.) | 3 | burns | 3 | burns | 2 | burns |
| tear length (cm) | 6 | | 3.5 | | 7 | |
| handle (ratings) | 0.5 | 0 | 2 | 0 | 2.5 | 0 |

The handle ratings show that the handle of the treated fabric is somewhat fuller than the handle of the untreated fabric.

Example 10

A cotton fabric (weight per unit area 140 g/m²) is padded with an aqueous liquor of the composition given in the following Table II, and is then dried at 150° C. for 5 minutes in a nozzle dryer. After drying, a test is carried out to determine the flameproofing effect in the manner described in Example 9. The tear strength of the fabric is subsequently measured according to SNV 198 461. The values correspond to the percentage tear strength relative to that of untreated material. The colour-difference values are ascertained according to DIN 6174 D 65/10. The higher the value the more severe the degree of yellowing. All the results are summarised in the following Table II.

TABLE II

| | Treated cotton fabric | Untreated cotton fabric |
| --- | --- | --- |
| g of 48% aqueous solution of the salt of the formula (17) according to Example 1 per liter of liquor | 208 | 0 |
| pH-value of the liquor | 3.1 | — |
| % coating of salt of the formula (17) after drying | 7.8 | 0 |
| fireproofness | | |
| burning time (sec.) | 2 | burns |
| tear length (cm) | 8 | |
| tear strength % | | |
| warp | 92 | 100 |
| weft | 88 | 100 |
| colour-difference values | 3.5 | 0 |

The colour-difference values show that the treated fabric yellows only slightly more than the untreated fabric.

Example 11

A cotton fabric (weight per unit area 140 g/m$^2$) is padded with an aqueous liquor of the composition given in the following Table III, and then dried for 5 minutes at 150° C. After drying, the fireproofing effect, the tear strength, the colour difference and the handle are tested in the manner described in Examples 9 and 10. The results are shown in the following Table III.

TABLE III

|  | Treated cotton fabric | Untreated cotton fabric |
| --- | --- | --- |
| g of 9.68% aqueous solution of the salt of the formula (4) according to Example 3 per liter of liquor | 1000 | 0 |
| pH-value of the liquor | 6.2 | — |
| % coating of salt of the formula (4) after drying | 7.8 | — |
| fireproofness |  |  |
| burning time (sec.) | 2 | burns |
| tear length (cm) | 5.5 |  |
| tear strength % |  |  |
| warp | 96 | 100 |
| weft | 91 | 100 |
| colour-difference values | 3.8 | 0 |
| handle (ratings) | 0.5 | 0 |

Similar results are obtained with the salts of any one of the formulae (8), (12) and (16).

Example 12

Various fabrics are padded with an aqueous liquor of the composition given in the following Table IV, and then dried at 80° C. for 30 minutes. After drying of the material, the fireproofing effect is tested in the manner described in Example 9. Also measured after drying is the degree of whiteness according to the CIBA/GEIGY white scale (cp. CIBA/GEIGY Rundschau 1973/1, pp. 23 to 24) (the lower the degree of whiteness the more severe the yellowing), and a further value determined, after drying and subsequent two-days' storage of the fabrics at 65% relative humidity, is the hygroscopicity of the treated fabrics on the basis of the increase in weight. The hygroscopicity is calculated as a percentage of the original weight of fabric. The results are summarised in the following Table IV.

TABLE IV

|  | Type and weight per unit area of the fabrics | | | |
| --- | --- | --- | --- | --- |
|  | polyacrylonitrile (138 g/m$^2$) | | polyester/cotton 50:50 (167 g/m$^2$) | |
|  | treated | untreated | treated | untreated |
| g of salt of the formula (6) according to Example 5 per liter of liquor | 270 | 0 | 300 | 0 |
| pH-value of the liquor | 8.8 | — | 8.8 | — |
| % coating of salt of the formula (6) after drying | 26.8 | — | 24.9 | — |
| fireproofness |  |  |  |  |
| burning time (sec.) | 2 | burns | 0 | burns |
| tear length (cm) | 8 |  | 4 |  |
| degree of whiteness | −44 | 15 | −33 | 68 |
| hygroscopicity (% water absorption) | 1.4 | 0.9 | 6.6 | 7.2 |

The measured results for the degree of whiteness show that treated fabric yellows only slightly more than untreated fabric.

Similar results are obtained with the salts of any one of the formulae (4), (8), (12) and (16).

Example 13

A cotton fabric (weight per unit area 140 g/m$^2$) is padded with an aqueous liquor of the composition given in the following Table V, and is subsequently dried at 150° C. for 5 minutes. After drying of the treated material, tests are carried out to determine the fireproofing effect, the tear strength, the degree of whiteness and the hygroscopicity in the manner indicated in Examples 9, 10 and 12. The results are summarised in the following Table V.

TABLE V

|  | Treated cotton fabric | | Untreated cotton fabric |
| --- | --- | --- | --- |
| g of salt of the formula (6) according to Example 5 per liter of liquor | 105 | 135 | 0 |
| pH-value of the liquor | 8.9 | 8.9 | — |
| % coating of salt of the formula (6) after drying | 6.6 | 9.7 | — |
| fireproofness |  |  |  |
| burning time (sec.) | 1 | 2 | burns |
| tear length (cm) | 7 | 6 |  |
| tear strength % |  |  |  |
| warp | 105 | 98 | 100 |
| weft | 92 | 97 | 100 |
| degree of whiteness | −9 | −25 | 67 |
| hygroscopicity (% absorption of water) | 6.8 | 6.8 | 7.4 |

Example 14

A polyacrylonitrile fabric (weight per unit area 138 g/m$^2$) is padded with an aqueous liquor of the composition shown in the following Table VI, and is then dried at 80° C. for 30 minutes. After drying of the material, the fireproofing effect is tested as given in Example 9. The results are summarized in the following Table VI.

TABLE VI

|  | Treated polyacrylonitrile fabric | Untreated polyacrylonitrile fabric |
| --- | --- | --- |
| g of 50% aqueous solution of the salt of the formula (13) according to Example 4 per liter of liquor | 500 | 0 |
| fireproofness |  |  |
| burning time (sec.) | 3 | burns |
| tear length (cm) | 4 |  |

Example 15

A cotton fabric (weight per unit area 140 g/m$^2$) is padded with an aqueous liquor of the composition shown in the following Table VII, and is then dried at 150° C. for 5 minutes. After drying of the material, the test to determine the fireproofing effect and the tear strength is carried out as given in Examples 9 and 10. The results are summarised in the Table VII which follows.

TABLE VII

| | Treated cotton fabric | Untreated cotton fabric |
|---|---|---|
| g of 50% aqueous solution of the salt of the formula (13) according to Example 4 per liter of liquor | 250 | 0 |
| fireproofness | | |
| burning time (sec.) | 1 | burns |
| tear length (cm) | 2.5 | |
| tear strength % | | |
| warp | 93 | 100 |
| weft | 88 | 100 |

Example 16

A polyester/cotton mixed fabric 50:50 (weight per unit area 167 g/m$^2$) is padded with an aqueous liquor of the composition shown in the following Table VIII, and is then dried at 150° C. for 5 minutes in a nozzle dryer. After drying of the material, the fireproofing effect is tested as given in Example 9, and the tear strength and colour difference values as given in Example 10. The results are summarised in the Table VIII which follows.

TABLE VIII

| | Treated polyester/ cotton mixed fabric | Untreated polyester/ cotton mixed fabric |
|---|---|---|
| g of salt of the formula (7) wherein y is 2, according to Example 8, per liter of liquor | 300 | 0 |
| pH-value of the liquor | 3.9 | — |
| % coating of salt | 20.2 | — |
| of the formula (7) wherein y is 2 after drying | | |
| fireproofness | | |
| burning time (sec) | 16 | burns |
| tear length (cm) | 5 | |
| tear strength % | | |
| warp | 95.7 | 100 |
| weft | 77.4 | 100 |
| colour-difference values | 2.4 | 0 |

What is claimed is:

1. A process for fireproofing organic fibers, comprising the step of applying to the fibers an aqueous solution of a phosphonic acid salt of the formula

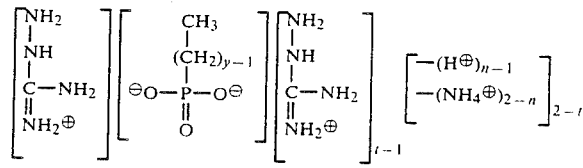

in which n, t and y are each 1 or 2.

2. The process of claim 1 wherein the aqueous solution is applied to the fibers by padding and the fibers are subsequently dried at a temperature in the range of 60° to 200° C.

3. The process of claim 1 wherein the aqueous solution contains 25 to 500 g/l of phosphonic acid salt.

4. The process according to claim 1 wherein the fibers are synthetic or cellulose or mixtures thereof.

5. The process of claim 1 wherein the fibers are polyacrylonitrile, polyester, polyester/cellulose or cellulose.

6. A textile bearing thereon a fire retardant finish conferred by the process of claim 1.

* * * * *